United States Patent
Tan et al.

(10) Patent No.: US 6,916,924 B2
(45) Date of Patent: Jul. 12, 2005

(54) PROCESS FOR SYNTHESIS OF HETEROARYL-SUBSTITUTED UREA COMPOUNDS USEFUL AS ANTIINFLAMMATORY AGENTS

(75) Inventors: Zhulin Tan, Danbury, CT (US); Jinhua J. Song, Hopewell Junction, NY (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 458 days.

(21) Appl. No.: 10/074,895

(22) Filed: Feb. 12, 2002

(65) Prior Publication Data

US 2002/0123631 A1 Sep. 5, 2002

Related U.S. Application Data

(60) Provisional application No. 60/268,841, filed on Feb. 15, 2001.

(51) Int. Cl.[7] .................. C07D 413/12; C07D 249/14; C07D 233/48; C07D 231/40
(52) U.S. Cl. ....................... 544/140; 548/251; 548/255; 548/262.8; 548/332.5; 548/371.7; 548/558
(58) Field of Search .................... 544/140; 548/251, 548/255, 262.8, 332.5, 371.7, 558, 266.4, 267.6

(56) References Cited

U.S. PATENT DOCUMENTS 6,080,763 A    6/2000    Regan et al.
6,319,921 B1   11/2001   Cirillo et al.

FOREIGN PATENT DOCUMENTS

WO    WO 00/55139 A3    9/2000
WO    WO 00/55139 A2    9/2000
WO    WO 01/90072    5/2001
WO    WO 01/04115    6/2001
WO    WO 01/32627    10/2001

OTHER PUBLICATIONS

International Search Report—May 7, 2002.
New Aryl/Heteroaryl C–N Bond Cross–coupling Reactions via Arylboronic Acid/Cupric Acetate Arylation Patrick Y.S. Lam, et al; Tetrahedron Letters 39, (1998) 2941–2944.
U.S. Appl. No. 09/902,085 filed Jul. 11. 2001, Kapadia, S. et al; A Novel Synthesis for Heteroarylamine Compounds.

*Primary Examiner*—Patricia L. Morris
(74) *Attorney, Agent, or Firm*—Michael P. Morris; Anthony P. Bottino; Philip I. Datlow

(57) ABSTRACT

This invention relates to novel processes for preparing heteroaryl-substituted urea compounds of formula (I):

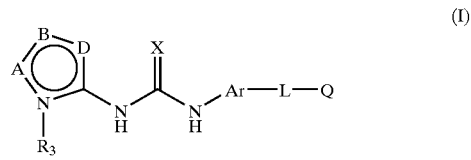

which are useful for treating diseases and pathological conditions involving inflammation such as chronic inflammatory disease. X, Ar, L, Q and

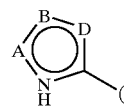

are described herein.

8 Claims, No Drawings

PROCESS FOR SYNTHESIS OF HETEROARYL-SUBSTITUTED UREA COMPOUNDS USEFUL AS ANTIINFLAMMATORY AGENTS

RELATED APPLICATION DATA

This application claims benefit to U.S. provisional application No. 60/268,841 filed Feb. 15, 2001.

TECHNICAL FIELD OF THE INVENTION

This invention relates to novel processes for preparing heteroaryl-substituted urea compounds of formula (I):

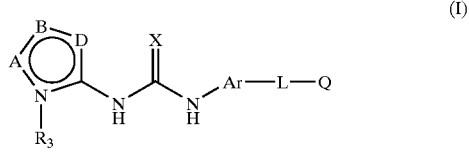

(I)

which are useful for treating diseases and pathological conditions involving inflammation such as chronic inflammatory disease. X, Ar, L, Q and

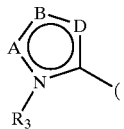

are described hereinbelow.

BACKGROUND OF THE INVENTION

Aryl- and heteroaryl-substituted ureas have been described as inhibitors of cytokine production and effective therapeutics in cytokine-mediated diseases including inflammatory and autoimmune diseases. Examples of such compounds are reported in U.S. Pat. Nos. 6,080,763 and 6,319,921, and WO 00/55139 including aryl- or heteroaryl-substituted ureas of the formula shown below:

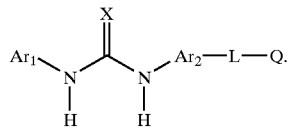

Among the favored $Ar_1$ are substituted or unsubstituted aryl or heteroaryl groups, including those defined below in this application.

A preferred step in the synthesis of this class of compounds is the formation of a urea bond as illustrated in Scheme I.

Scheme I

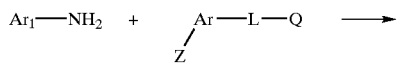

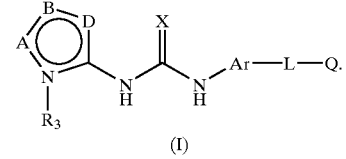

(I)

In Scheme I, Z can be an isocyanate or isothiocyanate or an amine (in which case the isocyanate or isothiocyanate is formed in situ) or Z can be $R_bOC(O)NH$ where $OR_b$ is a leaving group. The reaction may also be carried out in the reverse sense (i.e., $Ar_1$-Z+$H_2N$—Ar-L-Q).

U.S. application Ser. No. 09/611,109 discloses a method of making similar compounds by reacting a carbamate, made from reaction of a $Ar_1$—$NH_2$ and a haloformate, and the appropriate the amine as shown below to form the product compound:

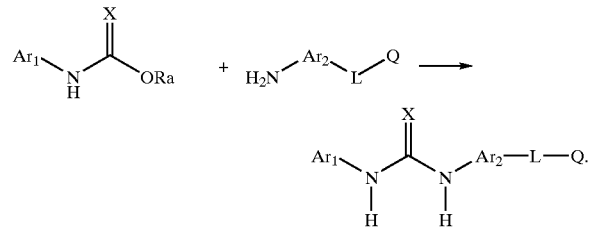

The methods previously described for the synthesis of (I) require the preparation of intermediate (II), where $Ar_1$ is the desired aryl or heteroaryl group. Preparation of (II) often requires a multi-step synthesis. For example the preferred intermediate (IIa) shown below is prepared by reaction of an aryl hydrazine with a ketonitrile. See also U.S. application Ser. Nos. 09/698,442, 09/902,085 and 09/735,160. Often, preferred aryl hydrazines and ketonitriles are not available commercially and must themselves be synthesized. This non-convergent approach also makes it inconvenient and tedious to prepare a series of analogs of formula (I) differing only in $R_3$:

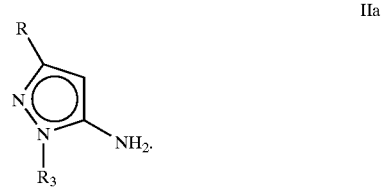

IIa

Recent reports in the chemical literature described improved methods for the coupling of aryl groups to NH-containing heterocycles. For example, P. Y. S. Lam et al. (Tetrahedron Letters, 1998, 2941) describes the coupling of aryl groups to NH-containing heterocycles in the presence of cupric acetate and base. The reaction occurs under mild conditions and is not air-sensitive. The reaction is successful with a variety of aryl boronic acids, many of which are commercially available.

In the novel process disclosed herein, $R_3$ is coupled to intermediate (Ia) in a final step.

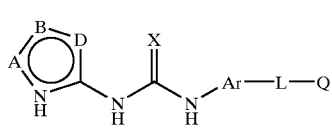

(Ia)

Intermediates required for the final coupling step of $R_3$ to Ia are often commercially available or readily prepared.

BRIEF SUMMARY OF THE INVENTION

It is therefore an object of this invention to provide a process for the preparation of the aryl- and heteroaryl-substituted urea compounds of the formula (I) shown below:

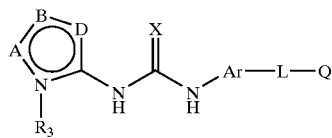

(I)

comprising the steps of:

1) reacting an intermediate compound of the formula (III) with a heteroarylamine compound of the formula (II), to form an intermediate compound of the formula (Ia). Suitable conditions and the definitions for X, Ar, L, Q and

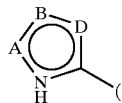

are described hereinbelow:

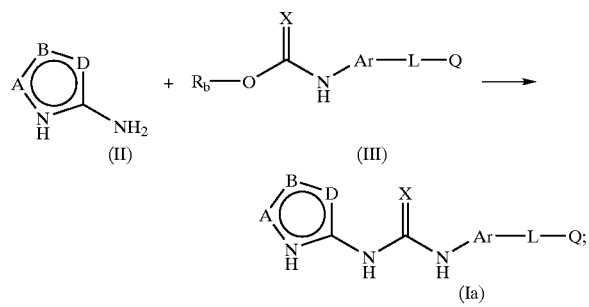

2) coupling the product of step 1), formula (Ia), with an electrophile Y—$R_3$, to form a compound of the formula (I). Suitable conditions and the definitions of Y and $R_3$ are described hereinbelow:

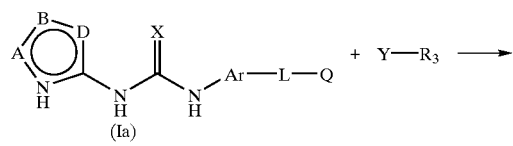

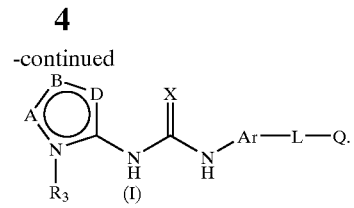

(I)

DETAILED DESCRIPTION OF THE INVENTION

The present invention is directed to the synthesis of compounds having the formula (I):

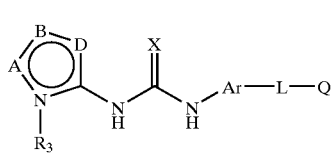

(I)

said process comprising:

1) reacting an intermediate compound of the formula (III) with a heteroarylamine compound of the formula (II), said reaction occuring in the presence of a suitable base such as triethylamine, diisopropylethylamine, N-methylpyrrolidine, DBU, DMAP, N-methylmorpholine, pyridine or methyl pyridine, preferably diisopropylethylamine;

and in a suitable organic solvent, preferably a polar non-protic organic solvent selected from NMP, acetonitrile, DMF, DMAC and DMSO, preferably DMSO; and at a suitable temperature of about 40–100° C., preferably about 80° C. for a reaction time of about 1 to 20 hours, preferably 4–10 hours, to form an intermediate compound of the formula (Ia):

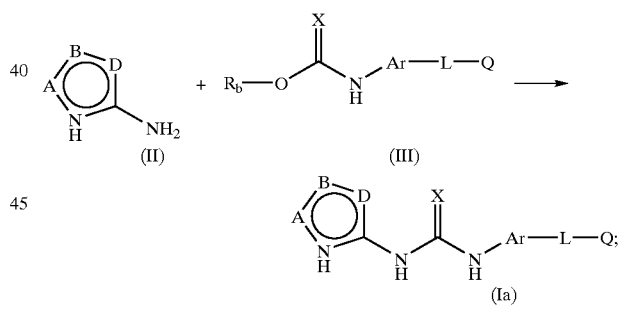

wherein $R_b$ represents a group that renders Rb—O— a leaving group, for example aryl such as phenyl or a $C_{2-3}$ halocarbon, such as 2,2,2-trichloroethyl, preferably $R_b$ is 2,2,2-trichloroethyl. Certain (II) are either available or can be obtained by known methods, reference in this regard may be made to U.S. Pat. No. 6,319,921, U.S. application Ser. Nos. 09/505,582, 09/698,442, 09/902, 085 and 09/735,160, each incorporated herein by reference in their entirety.

2) coupling the product of step 1), formula (Ia), with electrophile Y—$R_3$, preferably present in about a two-fold molar excess, wherein the moiety Y is a group selected from $BR_2$, $BR_3M$, $SiR_3$ and $SnR_3$ wherein R is $C_{1-6}$alkyl, $C_{1-6}$alkoxy, hydroxy or halogen (the halogen is preferably fluorine) and wherein M is Na, Li or K, preferably Y is $B(OH)_2$, said coupling reaction occurring in the presence of a suitable base such as triethylamine or pyridine, preferably pyridine, preferably present in about a two-fold molar excess, and in the presence of a suitable catalyst such as Cu(OAc)₂, [Cu(OH).TMEDA]₂Cl₂ or CuCO₃.Cu(OH)₂, preferably Cu(OAC)₂, preferably present at about a 1.5 molar excess; and said coupling reaction occurring at a suitable temperature of about 20–30° C., in a suitable solvent such as methylene chloride, 1,4-dioxane, N-methylpyrrolidinone, THF and DMF, preferably, methylene chloride, to form a compound of the formula (I):

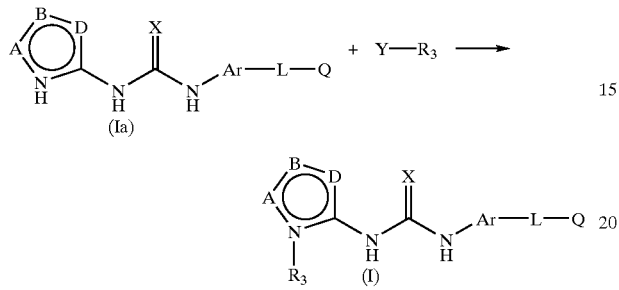

wherein:

the heteroaryl ring in formulas (I), (Ia) and (II):

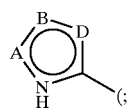

is chosen from:

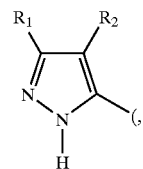
(a)

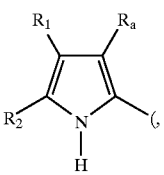
(b)

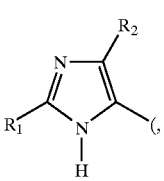
(c)

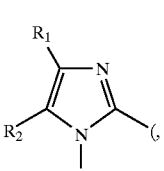
(d)

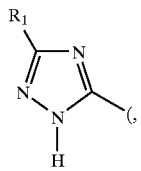
(e)

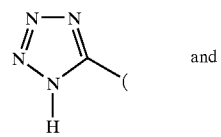
(f) and

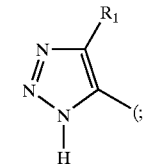
(g)

wherein for the above heteroaryl rings (a), (b) and (d), $R_1$ and $R_2$ or $R_a$ can join to form a benzo ring fused to the heterocyclic ring to form a bicyclic heteroaryl;

Ar is:
  phenyl, naphthyl, quinoline, isoquinoline, tetrahydronaphthyl, benzofuran, indanyl, indenyl or indole each being optionally substituted with one to three $R_2$ groups;

L, a linking group, is:
  a bond or a $C_{1-10}$ to saturated or unsaturated branched or unbranched carbon chain, wherein one or more C atoms are optionally replaced by O, N, or $S(O)_m$; and wherein L is optionally partially or fully halogenated and optionally independently substituted with one to two oxo groups, nitrile, phenyl or one or more $C_{1-4}$ alkyl optionally substituted by one or more halogen atoms;

or L is a cyclic group which is:
  a) a $C_{5-8}$ cycloalkyl or cycloalkenyl optionally substituted with 1–2 oxo groups, 1–3 $C_{1-4}$ branched or unbranched alkyl or $C_{1-4}$alkoxy;
  b) phenyl, furan, thiophene, pyridine, pyrimidine, pyridinone, dihydropyridinone, maleimide, dihydromaleimide or pyrazine each being optionally independently substituted with 1–3 $C_{1-4}$ branched or unbranched alkyl, $C_{1-4}$alkoxy, cyano, di-($C_{1-3}$ alkyl)amino, $C_{1-6}$alkyl-$S(O)_m$, or halogen;

wherein said cyclic group is optionally attached to a $C_{1-4}$ saturated or unsaturated branched or unbranched carbon chain wherein said carbon chain is in turn covalently attached to Q, said carbon chain is optionally partially or fully halogenated and wherein one or more methylene groups are optionally replaced by O, N, $S(O)_m$, wherein said methylene groups are further optionally independently substituted with 1–2 oxo groups and one or more $C_{1-4}$ branched or unbranched alkyl optionally substituted by one or more halogen atoms;

Methods for making 'L' are known in the art, and are also to be found in U.S. patent application Ser. Nos. 09/484,638 and 09/714,539.

Q is selected from the group consisting of:
a) phenyl, naphthyl, pyridine, pyrimidine, pyridazine, furan, thiophene, pyran, naphthyridine and oxazo[4,5-b]pyridine which are optionally substituted with one to three groups selected from the group consisting of halogen, $C_{1-6}$ alkyl, $C_{1-6}$ alkoxy, di-($C_{1-3}$ alkyl)amino and $C_{1-6}$ alkyl-S(O)$_m$;

b) tetrahydropyran, tetrahydrofuran, 1,3-dioxolanone, 1,3-dioxanone, 1,4-dioxane, N-morpholine, N-thiomorpholine, N-thiomorpholine sulfoxide, N-thiomorpholine sulfone, cyclohexanone, cyclohexanol, pentamethylene sulfide, pentamethylene sulfoxide, pentamethylene sulfone, tetramethylene sulfide, tetramethylene sulfoxide and tetramethylene sulfone which are optionally substituted with one to three groups selected from the group consisting of $C_{1-6}$ alky, $C_{1-6}$ alkoxy, di-($C_{1-3}$ alkyl)amino-$C_{1-3}$ alkyl, and $C_{1-3}$ alkoxy-$C_{1-3}$ alkyl;

c) $C_{1-6}$ alkoxy, tertiary amine wherein the amino nitrogen is covalently bonded to groups selected from the group consisting of $C_{1-3}$ alkyl and $C_{1-5}$ alkoxyalkyl and phenyl wherein the phenyl ring is optionally substituted with one to two groups selected from the group consisting of halogen, $C_{1-6}$ alkoxy, di-($C_{1-3}$ alkyl)amino, $C_{1-6}$ alkyl-S(O)$_m$ and phenyl-S(O)$_m$, wherein the phenyl ring is optionally substituted with one to two groups consisting of halogen, $C_{1-6}$ alkoxy, or di-($C_{1-3}$ alkyl)amino;

$R_1$ is selected from the group consisting of:
(a) $C_{3-10}$ branched or unbranched alkyl, which may optionally be partially or fully halogenated, and optionally substituted with one to three phenyl, naphthyl or heterocyclic groups selected from the group consisting of pyridinyl, pyrimidinyl, pyrazinyl, pyridazinyl, thienyl, furyl, isoxazolyl and isothiazolyl; each such phenyl, naphthyl or heterocycle selected from the group hereinabove described, being substituted with 0 to 5 groups selected from the group consisting of halogen, $C_{1-6}$ branched or unbranched alkyl which is optionally partially or fully halogenated, $C_{3-8}$ cycloalkyl, $C_{5-8}$ cycloalkenyl, cyano, $C_{1-3}$ alkyloxy which is optionally partially or fully halogenated and di($C_{1-3}$)alkylaminocarbonyl;

(b) $C_{3-7}$ cycloalkyl selected from the group consisting of cyclopropyl, cyclobutyl, cyclopentanyl, cyclohexanyl, cycloheptanyl, bicyclopentanyl, bicyclohexanyl and bicycloheptanyl, which are optionally partially or fully halogenated and optionally substituted with one to three $C_{1-3}$ alkyl groups, or an analog of such cycloalkyl group wherein one to three ring methylene groups are replaced by groups independently selected from O, S, >C=O and >C=S;

(c) $C_{3-10}$ branched alkenyl optionally partially or fully halogenated, and optionally substituted with one to three $C_{1-5}$ branched or unbranched alkyl, phenyl, naphthyl or heterocyclic groups, with each such heterocyclic group being independently selected from the group consisting of pyridinyl, pyrimidinyl, pyrazinyl, pyridazinyl, thienyl, furyl, isoxazolyl and isothiazolyl, and each such phenyl, naphthyl or heterocyclic group being substituted with 0 to 5 groups selected from halogen, $C_{1-6}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl, bicycloheptanyl, cyano, $C_{1-3}$ alkyloxy which is optionally partially or fully halogenated and di($C_{1-3}$)alkylaminocarbonyl;

(d) $C_{5-7}$ cycloalkenyl selected from the group consisting of cyclopentenyl, cyclohexenyl, cyclohexadienyl, cycloheptenyl, cycloheptadienyl, bicyclohexenyl and bicycloheptenyl, wherein such cycloalkenyl group is optionally substituted with one to three $C_{1-3}$ alkyl groups;

(e) cyano; and,
(f) methoxycarbonyl, ethoxycarbonyl and propoxycarbonyl;

$R_2$ is selected from the group consisting of:
a $C_{1-6}$ branched or unbranched alkyl optionally partially or fully halogenated, acetyl, aroyl, $C_{1-4}$ branched or unbranched alkoxy optionally partially or fully halogenated, halogen and methoxycarbonyl;

$R_3$ is selected from the group consisting of:
a) a phenyl, naphthyl or heteroaryl group selected from the group consisting of pyridinyl, pyrimidinyl, pyrazinyl, pyridazinyl, thienyl, furyl, tetrahydrofuryl, isoxazolyl, isothiazolyl, quinolinyl, isoquinolinyl, indolyl, benzofuranyl, benzoxazolyl, benzisoxazolyl, benzothiofuranyl, cinnolinyl, pterindinyl, phthalazinyl, naphthypyridinyl, quinoxalinyl, quinazolinyl, purinyl and indazolyl wherein such phenyl, naphthyl or heteroaryl group is optionally substituted with one to five groups selected from the group consisting of a $C_{1-6}$ branched or unbranched alkyl, phenyl, naphthyl, heteroaryl group selected from the groups hereinabove described, $C_{1-6}$ branched or unbranched alkyl which is optionally partially or fuilly halogenated, cyclopropyl, cyclobutyl, cyclopentanyl, cyclohexanyl, cycloheptanyl, bicyclopentanyl, bicyclohexanyl, bicycloheptanyl, phenyl $C_{1-5}$ alkyl, naphthyl $C_{1-5}$ alkyl, halo, cyano, $C_{1-3}$ alkyloxy which may optionally be partially or fuilly halogenated, phenyloxy, naphthyloxy, beteraryloxy wherein the heterocyclic moiety is selected from the group hereinabove described, nitro, di-($C_{1-3}$)alkylamino, di-($C_{1-3}$)alkyl aminocarbonyl, $C_{1-5}$ alkyl-C(O)—$C_{1-4}$ alkyl, di-($C_{1-3}$) alkylamino-$C_{1-5}$ alkyl, di-($C_{1-3}$)alkylamino-S(O)$_2$, $R_4$—$C_{1-5}$ alkyl, $R_5$—$C_{1-5}$ alkoxy, $R_6$—C(O)—$C_{1-5}$ alkyl and $R_7$—$C_{1-5}$ alkyl-N($R_8$)—; and b) a fused aryl selected from the group consisting of benzocyclobutanyl indanyl, indenyl, dihydronaphthyl, tetrahydronaphthyl, benzocyclohептanyl and benzocycloheptenyl, or a fused heterocyclyl selected from cyclopentenopyridine, cyclohexanopyridine, cyclopentanopyrimidine, cyclohexanopyrimidine, cyclopentanopyrazine, cyclohexanopyrazine, cyclopentanopyridazine, cyclohexanopyridazine, cyclopentanoquinoline, cyclohexanoquinoline, cyclopentanoisoquinoline, cyclohexanoisoquinoline, cyclopentanoindole, cyclohexanoindole, cyclopentanobenzoxazole, cyclohexanobenzoxazole, cyclopentanothiophene and cyclohexanothiophene; wherein the fused aryl or fused heterocyclyl ring is substituted with 0 to 3 groups independently selected from phenyl, naphthyl, heterocyclyl selected from the group consisting of pyridinyl, pyrimidinyl, pyrazinyl, pyridazinyl, thienyl, furyl, isoxazolyl, and isothiazolyl, $C_{1-6}$ branched or unbranched alkyl which is optionally partially or fully halogenated, halo, cyano, $C_{1-3}$ alkyloxy which is optionally partially or fully halogenated, phenyloxy, naphthyloxy, heterocyclyloxy wherein the heterocyclyl moiety is selected from the group hereinabove described, nitro, di-($C_{1-3}$)alkylamino, di-($C_{1-3}$) alkyl aminocarbonyl, $C_{1-4}$ alkyl-OC(O), $C_{1-5}$ alkyl-C(O)—$C_{1-4}$ branched or unbranched alkyl, di-($C_{1-3}$) alkylamino-$C_{1-5}$ alkyl, $R_9$—$C_{1-5}$ alkyl, $R_{10}$—$C_{1-5}$ alkoxy, $R_{11}$—C(O)—$C_{1-5}$ alkyl and $R_{12}$—$C_{1-5}$ alkyl-N($R_{13}$)—;

$R_1$ and $R_2$ taken together optionally form a fused phenyl or pyridinyl ring;

each $R_8$ or $R_{13}$ is independently $C_{1-4}$ branched or unbranched alkyl optionally partially or fully halogenated;

each $R_4, R_5, R_6, R_7, R_9, R_{10}, R_{11}$ and $R_{12}$ is independently selected from the group consisting of:

N-morpholine and piperazine;

$R_a$ equals the definitions of $R_1$, wherein $R_a$ and $R_1$ can be simultaneously the same or different;

each m is independently 0, 1 or 2;

X is O or S;

and if Ar, L, Q or $R_1$ through $R_{13}$ contains group, such as NH, $NH_2$ or OH, that could react during the urea formation (step 1) or coupling step (step 2) one may employ protection and deprotection chemistry known in the art to mask these groups during these steps.

Particular work-up and purification methods depending on the compound desired will be apparent to those of ordinary skill in the art. A preferred method is shown in Example 1 in the present specification.

A preferred subgeneric aspect of the invention comprises a process of producing compounds of the formula(I) wherein Ar is naphthyl, tetrahydronaphthyl, indanyl or indenyl.

A more preferred subgeneric aspect of the invention comprises a process of producing compounds of the formula (I) wherein Ar is naphthyl.

A yet more preferred subgeneric aspect of the invention comprises a process of producing compounds of the formula (I), as described in the immediate previous paragraph, wherein:

the heteroaryl ring

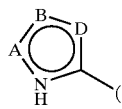

is:

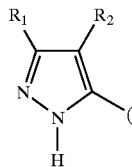 or 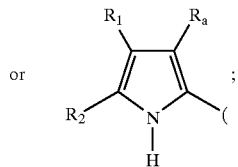;

Ar is 1-naphthyl;

L is $C_{1-6}$ saturated or unsaturated branched or unbranched carbon chain wherein one or more C atoms are optionally replaced by O, N or $S(O)_m$; and wherein said linking group is optionally substituted with one to two oxo groups, $C_{1-4}$ alkyl optionally substituted by one or more halogen atoms; or L is cyclopentenyl, cyclohexenyl, cycloheptenyl, each optionally substituted with an oxo group or 1–3 $C_{1-4}$ branched or unbranched alkyl or $C_{1-4}$alkoxy; or L is phenyl, pyridine, furan or thiophene each being optionally independently substituted with 1–3 $C_{1-4}$ branched or unbranched alkyl, $C_{1-4}$alkoxy, cyano, di-($C_{1-3}$ alkyl) amino, $C_{1-6}$ alkyl-$S(O)_m$ or halogen;

wherein said cyclic group is optionally attached to a $C_{1-4}$ saturated or unbranched or unbranched carbon chain wherein said carbon chain is in turn covalently attached to Q, said carbon chain is optionally partially or fully halogenated and wherein one or more methylene groups are optionally replaced by O, N or $S(O)_m$, wherein said methylene groups are further optionally independently substituted with 1–2 oxo groups and one or more $C_{1-4}$ branched or unbranched alkyl optionally substituted by one or more halogen atoms;

$R_1$ is $C_{3-4}$alkyl branched or unbranched, cyclopropyl or cyclohexanyl optionally partially or fully halogenated and optionally substituted with one to three $C_{1-3}$ alkyl groups;

$R_3$ is selected from the group consisting of phenyl, pyridinyl each being optionally substituted with one to five groups selected from the group consisting of a $C_{1-6}$ branched or unbranched alkyl, phenyl, naphthyl, pyridinyl, $C_{1-6}$ branched or unbranched alkyl, cyclopropyl, cyclobutyl, cyclopentanyl, cyclohexanyl, cycloheptanyl, bicyclopentanyl, bicyclohexanyl, bicycloheptanyl, phenyl $C_{1-5}$ alkyl, naphthyl $C_{1-5}$ alkyl, halo, cyano, $C_{1-3}$ alkyloxy which may optionally be partially or fully halogenated, phenyloxy, naphthyloxy, pyridinyloxy, nitro, di-($C_{1-3}$)alkylamino, di-($C_{1-3}$)alkyl aminocarbonyl, $C_{1-5}$ alkyl-C(O)—$C_{1-4}$ alkyl, di-($C_{1-3}$) alkylamino-$C_{1-5}$ alkyl, di-($C_{1-3}$)alkylamino-$S(O)_2$, $R_4$—$C_{1-5}$alkyl, $R_5$—$C_{1-5}$ alkoxy, $R_6$—C(O)—$C_{1-5}$ alkyl and $R_7$—$C_{1-5}$ alkyl-$N(R_8)$—.

A yet further preferred subgeneric aspect of the invention comprises a process of producing compounds of the formula (I), as described in the immediate previous paragraph, wherein the heteroaryl ring

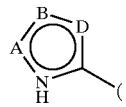

is:

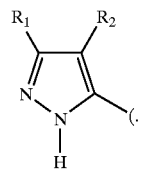

A still yet further preferred subgeneric aspect of the invention comprises a process of producing compounds of the formula (I), as described in the immediate previous paragraph, wherein L is $C_{1-5}$ saturated carbon chain wherein one or more C atoms are optionally independently replaced by O, N or $S(O)_m$; and wherein said linking group is optionally substituted with 0–2 oxo groups and one or more $C_{1-4}$ branched or unbranched alkyl optionally substituted by one or more halogen atoms;

More particularly preferred embodiments of the process of the invention is where L is L is:

O—$CH_2$, O—$CH_2CH_2$, O—$CH_2CH_2CH_2$, O—$CH_2CH_2$ ($CH_3$), O—$CH_2(CH_3)CH_2$, $S(O)_mCH_2$, $S(O)_mCH_2CH_2$, $S(O)_mCH_2CH_2CH_2$, $CH_2$, $CH_2CH_2$, $CH_2CH_2CH_2$, O—$CH_2C(O)$, HC≡C—$CH_2$ or HC≡C—$CH_2O$;

and Q is N-morpholino.

A even more particularly preferred embodiment of L is O—$CH_2CH_2$.

In all the compounds disclosed herein above in this application, in the event the nomenclature is in conflict with the structure, it shall be understood that the compound is defined by the structure.

The compounds produced by the novel process of the invention may be prepared as physiologically and pharmaceutically acceptable salts, as may seem appropriate to one of ordinary skill in the art.

The compounds produced by the novel process of the invention are only those which are contemplated to be 'chemically stable' as will be appreciated by those skilled in the art. For example, a compound which would have a 'dangling valency', or a 'carbanion' are not compounds contemplated to be made by the novel process.

All terms as used herein in this specification, unless otherwise stated, shall be understood in their ordinary meaning as known in the art. For example, "$C_{1-4}$alkoxy" is a $C_{1-4}$alkyl with a terminal oxygen, such as methoxy, ethoxy, propoxy, pentoxy and hexoxy. All alkyl, alkenyl and alkynyl groups shall be understood as being branched or unbranched where structurally possible and unless otherwise specified. Other more specific definitions are as follows:

In all alkyl groups or carbon chains within cycloalkyl groups, where one or more carbon atoms/methylene groups are optionally replaced by heteroatoms: O, S or N, it shall be understood that if N is riot substituted then it is NH, it shall also be understood that the heteroatoms may replace either terminal carbon atoms or internal carbon atoms within a branched or unbranched carbon chain.

Substitution on a carbon such as a methylene carbon by groups such as oxo result in definitions such as: alkoxycarbonyl, acyl, and amido, or if substituted on a can, for example, replace a methylene group —CH$_2$— with a carbonyl >C=O.

The term "halogen" as used in the present specification shall be understood to mean bromine, chlorine, fluorine or iodine. The definitions "partially or fully halogenated" "substituted by one or more halogen atoms" includes for example, mono, di or tri halo derivatives on one or more carbon atoms. A non-limiting example would be a halogenated alkyl such as —CH$_2$CHF$_2$, —CF$_3$ etc.

The term "aroyl" as used in the present specification shall be understood to mean "benzoyl" or "naphthoyl".

OMe: methoxy;
NMP: 1-methyl-2-pyrrolidinone;
THF: tetrahydrofuran;
DMF: N,N'-dimethylformamide;
DMAC: N-N'-dimethylacetamide;
DMSO: dimethylsulfoxide;
DMAP: 4-dimethylaminopyridine;
DBU: 1,8-diazabicyclo[5.4.0]undec-7-ene;
EtOAc: ethyl acetate
EtOH: ethanol
TMEDA: N,N,N',N'-tetramethylethylenediamine In order that this invention be more fully understood, the following examples are set forth. These examples are for the purpose of illustrating preferred embodiments of this invention, and are not to be construed as limiting the scope of the invention in any way.

SYNTHETIC EXAMPLES

Example 1

Synthesis of 1(5-tert-Butyl-2-phenyl-2H-pyrazol-3-yl)-3-[4-(2-morpholin-4-yl-ethoxy)naphthalen-1-yl]-urea

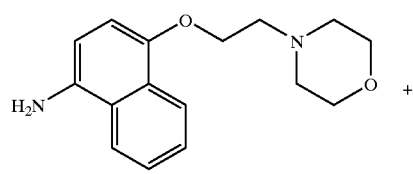

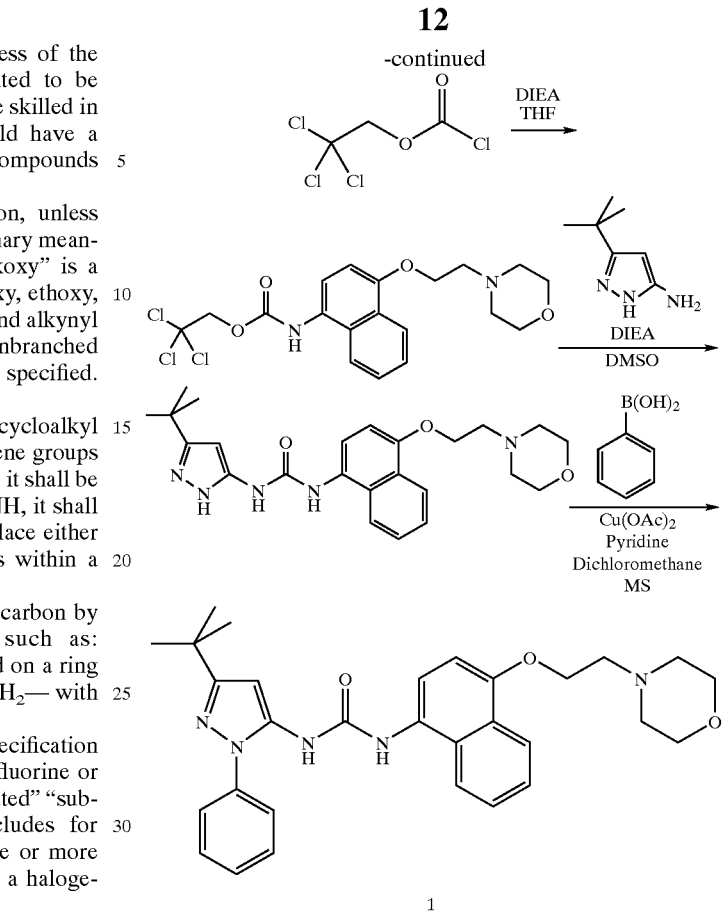

To a solution of 4-(2-morpholin-4-yl-ethoxy)-naphthalen-1-ylamine (10.9 g, 40 mmol) and N,N-diisopropylethylamine (10 mL) in THF (80 mL), cooled to −10° C. under argon, was added 2,2,2-trichloroethyl chloroformate (5.6 mL, 40 mmol) via syringe over 10 min. Upon stirring at −10° C. for 40 min, EtOAc (100 mL) and water (100 mL) were added. The organic layer was washed with brine, dried (MgSO$_4$), filtered and concentrated in vacuo. The crude product was triturated (ether), filtered, washed (ether) and air-dried to give a first crop as a slightly pink white solid (11.1 g). The filtrate was concentrated in vacuo, triturated (ether), filtered, washed (ether) and dried, providing a second crop of 4.6 g. A total of 15.7 g (88%) of [4-(2-morpholin-4-yl-ethoxy)-naphthalen-1-yl]-carbamic acid 2,2,2-trichloroethyl ester, was obtained as a pink solid, m.p. 124–125° C.; $^1$H NMR (CDCl$_3$) δ 2.66(t, 4H), 2.97(t, 2H), 3.75(t, 4H), 4.31(t, 3H), 4.88(s, 2H), 6.80(d, 1H), 6.94(s, 1H), 7.58(m, 3H), 7.87(d, 1H), 8.29(d, 1H); MS (CI) 447(M$^+$+H).

A solution of the above trichloroethyl carbamate (4.5 g, 10 mmol), (5-tert-butyl-2-aminopyrazole 1.4 g, 10 mmol), and N,N-diisopropylcthylamine (1.8 mL, 10 mmol) in DMSO (100 mL) was heated at 80° C. for 14 h. The mixture was cooled to room temperature, EtOAc (100 mL) and water (100 mL) were added. The organic layer was washed with brine, dried (MgSO$_4$), filtered, concentrated in vacuo, triturated (ether), washed (hexane) and dried in air to give 1-(5-tert-butyl-2H-pyrazol-3-yl)-3-[4-(2-morpholin-4-yl-ethoxy)-naphthalen-1-yl]-urea as a pale pink solid (3.7 g, 84%), mp 206–207° C., $^1$H NMR (DMSO) δ 1.25(s, 9H), 2.53(t, 4H), 2.83(t, 2H), 3.58(t, 4H), 4.25(t, 2H), 5.87(s, 1H), 6.96(d, 1H), 7.56(m, 2H), 7.82(d, 1H), 8.03(d, 1H), 8.18(d, 1H), 9.17(s, 1H), 12.06(s, 1H); MS (CI) 438(M$^+$+H).

A mixture of the above urea (0.022 g, 0.050 mmol), phenylboronic acid (0.012 g, 0.1 mmol), copper (II) acetate (0.014 g, 0.075 mmol), pyridine (0.01 mL, 0.1 mmol) and molecular sieves (4 Å activated, 0.030 g) in methylene chloride (2 mL) was stirred at room temperature for 14 h under air. After filtration through diatomaceous earth, the filtrate was concentrated in vacuo and purified by flash chromatography (EtOAc 100% to EtOH 100%) to give the title compound as a yellow-white solid (0.02 g, 73%), mp 142–143° C.; $^1$H NMR (DMSO) δ 1.26(s, 9H), 2.53(t, 4H) 2.83(t, 2H), 3.57(t, 4H), 4.24(t, 2H), 6.34(s, 1H), 6.94(d, 1H), 7.40(d, 1H), 7.55(m, 7H), 7.90(d, 1H), 8.15(d, 1H), 8.82(s, 1H), 8.92(s, 1H); MS (CI) 514(M$^+$+H).

Example 2

Synthesis of 1-(5-tert-Butyl-2-p-tolyl-2H-pyrazol-3-yl)-3-[4-(2-morpholin-4-yl-ethoxy)-naphthalen-1-yl]-urea

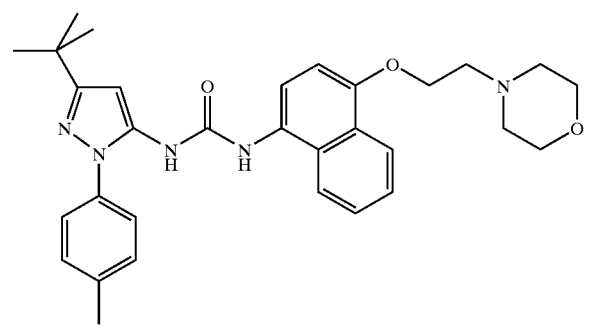

The title compound was prepared as described in the final step of Example 1 from 1-(5-tert-butyl-2H-pyrazol-3-yl)-3-[4-(2-morpholin-4-yl-ethoxy)-naphthalen-1-yl]-urea (0.022 g, 0.050 mmol), and p-tolylboronic acid (0.014 g, 0.1 mmol), using copper (II) acetate (0.014 g, 0.075 mmol), pyridine (0.01 mL, 0.1 mmol), molecular sieves (4 Å activated, 0.030 g) and methylene chloride (2 mL). The title compound was obtained as a yellow-white solid (0.013 g, 50%), mp 144–146° C.; $^1$H NMR (DMSO) δ 1.26(s, 9H), 2.36(s, 3H), 2.53(t, 4H) 2.82(t, 2H), 3.52(t, 4H), 4.23(t, 2H), 6.32(s, 1H), 6.94(d, 1H), 7.33(d, 1H), 7.42(d, 1H), 7.54(m, 3H), 7.90(d, 1H), 8.15(d, 1H), 8.18(d, 1H), 8.82(s, 1H), 8.96(s, 1H); MS (CI) 528(M$^+$+H).

What is claimed is:

1. A process of making a compound of the formula (I):

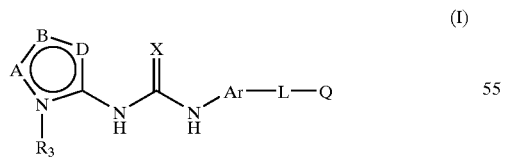

said process comprising:
1) reacting an intermediate compound of the formula (III) with a heteroarylamine compound of the formula (II), said reaction occuring in the presence of a base, in a polar non-protic organic solvent and at a temperature of about 40–100° C. for a reaction time of about 1 to 20 hours, to form an intermediate compound of the formula (Ia):

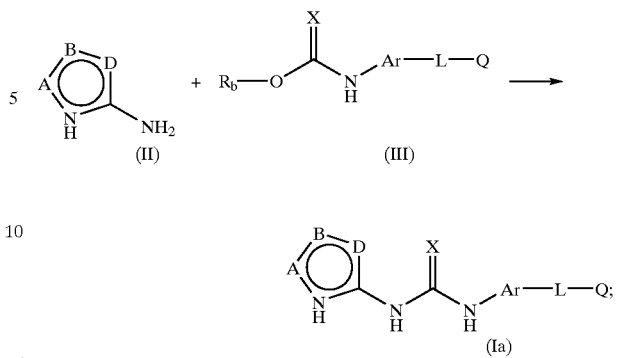

wherein $R_b$ represents phenyl or a $C_{2-3}$ halocarbon;

2) coupling the product of step 1), formula (Ia), with electrophile Y—R$_3$, wherein the moiety Y is a group selected from BR$_2$, BR$_3$M, SiR$_3$ and SnR$_3$ wherein R is $C_{1-6}$alkyl, $C_{1-6}$alkoxy, hydroxy or halogen and wherein M is Na, Li or K, said coupling reaction occuring in a base, and in the presence of a catalyst; and said coupling reaction occurring at a temperature of about 20–30° C., in a solvent, to form a compound of the formula (I):

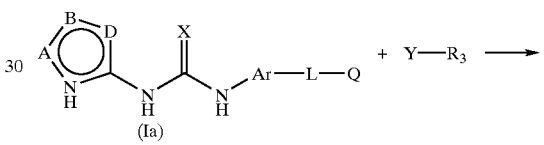

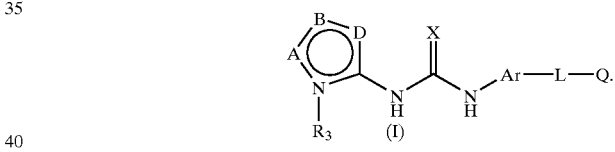

wherein:
the heteroaryl ring in formulas (Ia) and (II):

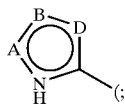

is chosen from:

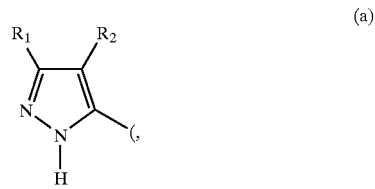

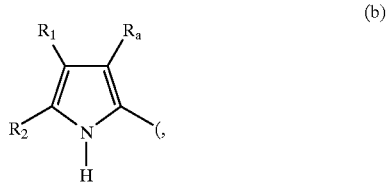

-continued

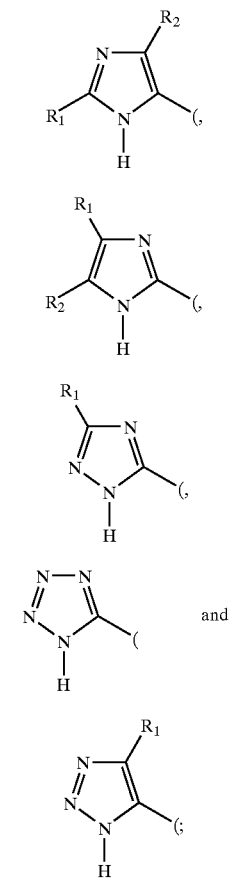

wherein for the above heteroaryl rings (a), (b) and (d), $R_1$ and $R_2$ or $R_a$ can join to form a benzo ring fused to the heterocyclic ring to form a bicyclic heteroaryl;

Ar is:

phenyl, naphthyl, quinoline, isoquinoline, tetrahydronaphthyl, benzofuran, indanyl, indenyl or indole each being optionally substituted with one to three $R_2$ groups;

L, a linking group, is:

a bond or a $C_{1-10}$ saturated or unsaturated branched or unbranched carbon chain, wherein one or more C atoms are optionally replaced by O, N, or $S(O)_m$; and wherein L is optionally partially or fully halogenated and optionally independently substituted with one to two oxo groups, nitrile, phenyl or one or more $C_{1-4}$ alkyl optionally substituted by one or more halogen atoms;

or L is a cyclic group which is:

a) a $C_{5-8}$ cycloalkyl or cycloalkenyl optionally substituted with 1–2 oxo groups, 1–3 $C_{1-4}$ branched or unbranched alkyl or $C_{1-4}$ alkoxy;

b) phenyl, furan, thiophene, pyridine, pyrimidine, pyridinone, dihydropyridinone, maleimide, dihydromaleimide or pyrazine each being optionally independently substituted with 1–3 $C_{1-4}$ branched or unbranched alkyl, $C_{1-4}$alkoxy, cyano, di-($C_{1-3}$ alkyl) amino, $C_{1-6}$ alkyl-$S(O)_m$, or halogen;

wherein said cyclic group is optionally attached to a $C_{1-4}$ saturated or unbranched or unbranched carbon chain wherein said carbon chain is in turn covalently attached to Q, said carbon chain is optionally partially or fully halogenated and wherein one or more methylene groups are optionally replaced by O, N, $S(O)_m$, wherein said methylene groups are further optionally independently substituted with 1–2 oxo groups and one or more $C_{1-4}$ branched or unbranched alkyl optionally substituted by one or more halogen atoms;

Q is selected from the group consisting of:

phenyl, naphthyl, pyridine, pyrimidine, pyridazine, furan, thiophene, pyran, naphthyridine and oxazo[4,5-b] pyridine which are optionally substituted with one to three groups selected from the group consisting of halogen, $C_{1-6}$ alkyl, $C_{1-6}$ alkoxy, di-($C_{1-3}$ alkyl)amino and $C_{1-6}$ alkyl-$S(O)_m$;

tetrahydropyran, tetrahydrofuran, 1,3-dioxolanone, 1,3-dioxanone, 1,4-dioxane, N-morpholine, N-thiomorpholine, N-thiomorpholine sulfoxide, N-thiomorpholine sulfone, cyclohexanone, cyclohexanol, pentamethylene sulfide, pentamethylene sulfoxide, pentamethylene sulfone, tetramethylene sulfide, tetramethylene sulfoxide and tetramethylene sulfone which are optionally substituted with one to three groups selected from the group consisting of $C_{1-6}$ alkyl, $C_{1-6}$ alkoxy, di-$Cl_{3}$ alkyl)amino-$C_{1-3}$ alkyl, and $C_{1-3}$ alkoxy-$C_{1-3}$ alkyl;

$C_{1-6}$ alkoxy, tertiary amine wherein the amino nitrogen is covalently bonded to groups selected from the group consisting of $C_{1-3}$ alkyl and $C_{1-5}$ alkoxyalkyl and phenyl wherein the phenyl ring is optionally substituted with one to two groups selected from the group consisting of halogen, $C_{1-6}$ alkoxy, di-$C_{1-3}$ alkyl)amino, $C_{1-6}$ alkyl-$S(O)_m$ and phenyl-$S(O)_m$, wherein the phenyl ring is optionally substituted with one to two groups consisting of halogen, $C_{1-6}$ alkoxy, or di-($C_{1-3}$ alkyl) amino;

$R_1$ is selected from the group consisting of:

$C_{3-10}$ branched or unbranched alkyl, which may optionally be partially or fully halogenated, and optionally substituted with one to three phenyl, naphthyl or heterocyclic groups selected from the group consisting of pyridinyl, pyrimidinyl, pyrazinyl, pyridazinyl, thienyl, furyl, isoxazolyl and isothiazolyl; each such phenyl, naphthyl or heterocycle selected from the group hereinabove described, being substituted with 0 to 5 groups selected from the group consisting of halogen, $C_{1-6}$ branched or unbranched alkyl which is optionally partially or fully halogenated, $C_{3-8}$ cycloalkyl, $C_{5-8}$ cycloalkenyl, cyano, $C_{1-3}$ alkyloxy which is optionally partially or fully halogenated and di($C_{1-3}$)alkylaminocarbonyl;

$C_{3-7}$ cycloalkyl selected from the group consisting of cyclopropyl, cyclobutyl, cyclopentanyl, cyclohexanyl, cycloheptanyl, bicyclopentanyl, bicyclohexanyl and bicycloheptanyl, which are optionally partially or fully halogenated and optionally substituted with one to three $C_{1-3}$ alkyl groups, or an analog of such cycloalkyl group wherein one to three ring methylene groups are replaced by groups independently selected from O, S, >C=O and >C=S;

$C_{3-10}$ branched alkenyl optionally partially or fully halogenated, and optionally substituted with one to three $C_{1-5}$ branched or unbranched alkyl, phenyl, naphthyl or heterocyclic groups, with each such heterocyclic group being independently selected from the group consisting of pyridinyl, pyrimidinyl, pyrazinyl, pyridazinyl, thienyl, furyl, isoxazolyl and isothiazolyl, and each such phenyl, naphthyl or heterocyclic group being substituted with 0 to 5 groups selected from halogen, $C_{1-6}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl, bicycloheptanyl, cyano, $C_{1-3}$ alkyloxy which is optionally partially or fully halogenated and di($C_{1-3}$) alkylaminocarbonyl;

$C_{5-7}$ cycloalkenyl selected from the group consisting of cyclopentenyl, cyclohexenyl, cyclohexadienyl, cycloheptenyl, cycloheptadienyl, bicyclohexenyl and bicycloheptenyl, wherein such cycloalkenyl group is optionally substituted with one to three $C_{1-3}$ alkyl groups;

cyano; and, methoxycarbonyl, ethoxycarbonyl and propoxycarbonyl;

$R_2$ is selected from the group consisting of:

a $C_{1-6}$ branched or unbranched alkyl optionally partially or fully halogenated, acetyl, aroyl, $C_{1-4}$ branched or unbranched alkoxy optionally partially or fully halogenated, halogen and methoxycarbonyl;

$R_3$ is selected from the group consisting of:

a phenyl, naphthyl or heteroaryl group selected from the group consisting of pyridinyl, pyrimidinyl, pyrazinyl, pyridazinyl, thienyl, furyl, tetrahydrofuryl, isoxazolyl, isothiazolyl, quinolinyl, isoquinolinyl, indolyl, benzofuranyl, benzoxazolyl, benzisoxazolyl, benzothiofuranyl, cinnolinyl, pterindinyl, phthalazinyl, naphthypyridinyl, quinoxalinyl, quinazolinyl, purinyl and indazolyl wherein such phenyl, naphthyl or heteroaryl group is optionally substituted with one to five groups selected from the group consisting of a $C_{1-6}$ branched or unbranched alkyl, phenyl, naphthyl, heteroaryl group selected from the groups hereinabove described, $C_{1-6}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl, bicycloheptanyl, phenyl $C_{1-5}$ alkyl, naphthyl $C_{1-5}$ alkyl, halo, cyano, $C_{1-3}$ alkyloxy which may optionally be partially or fully halogenated, phenyloxy, naphthyloxy, heteraryloxy wherein the heterocyclic moiety is selected from the group hereinabove described, nitro, di-($C_{1-3}$)alkylamino, di-($C_{1-3}$)alkyl aminocarbonyl, $C_{1-5}$ alkyl-C(O)—$C_{1-4}$ alkyl, di-($C_{1-3}$)alkylamino-$C_{1-5}$ alkyl, , di-($C_{1-3}$)alkylamino-S(O)$_2$, $R_4$—$C_{1-5}$ alkyl, $R_5$—$C_{1-5}$ alkoxy, $R_6$—C(O)—$C_{1-5}$ alkyl and $R_7$—$C_{1-5}$ alkyl-N($R_8$)—; and a fused aryl selected from the group consisting of benzocyclobutanyl, indanyl, indenyl, dihydronaphthyl, tetrahydronaphthyl, benzocycloheptanyl and benzocycloheptenyl, or a fused heterocyclyl selected from cyclopentenopyridine, cyclohexanopyridine, cyclopentanopyrimidine, cyclohexanopyrimidine, cyclopentanopyrazine, cyclohexanopyrazine, cyclopentanopyridazine, cyclohexanopyridazine, cyclopentanoquinoline, cyclohexanoquinoline, cyclopentanoisoquinoline, cyclohexanoisoquinoline, cyclopentanoindole, cyclohexanoindole, cyclopentanobenzoxazole, cyclohexanobenzoxazole, cyclopentanothiophene and cyclohexanothiophene; wherein the fused aryl or fused heterocyclyl ring is substituted with 0 to 3 groups independently selected from phenyl, naphthyl, heterocyclyl selected from the group consisting of pyridinyl, pyrimidinyl, pyrazinyl, pyridazinyl, thienyl, furyl, isoxazolyl, and isothiazolyl, $C_{1-6}$ branched or unbranched alkyl which is optionally partially or fully halogenated, halo, cyano, $C_{1-3}$ alkyloxy which is optionally partially or fully halogenated, phenyloxy, naphthyloxy, heterocyclyloxy wherein the heterocyclyl moiety is selected from the group hereinabove described, nitro, di-($C_{1-3}$)alkylamino, di-($C_{1-3}$) alkyl aminocarbonyl, $C_{1-4}$ alkyl-OC(O), $C_{1-5}$ alkyl-C(O)—$C_{1-4}$ branched or unbranched alkyl, di-($C_{1-3}$) alkylamino-$C_{1-5}$ alkyl, $R_9$—$C_{1-5}$ alkyl, $R_{10}$—$C_{1-5}$ alkoxy, $R_{11}$—C(O)—$C_{1-5}$ alkyl and $R_{12}$—$C_{1-5}$ alkyl-N($R_{13}$)—;

$R_1$ and $R_2$ taken together optionally form a fused phenyl or pyridinyl ring;

each $R_8$ or $R_{13}$ is independently $C_{1-4}$ branched or unbranched alkyl optionally partially or fully halogenated;

each $R_4$, $R_5$, $R_6$, $R_7$, $R_9$, $R_{10}$, $R_{11}$, and $R_{12}$ is independently selected from the group consisting of:

N-morpholine and piperazine;

$R_a$ equals the definitions of $R_1$, wherein $R_a$ and $R_1$ can be simultaneously the same or different;

each m is independently 0, 1 or 2;

X is O or S.

2. The process according to claim 1 wherein wherein Ar is naphthyl, tetrahydronaphthyl, indanyl or indenyl.

3. The process according to claim 2 wherein Ar is naphthyl.

4. The process according to claim 3 wherein the heteroaryl ring

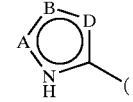

is:

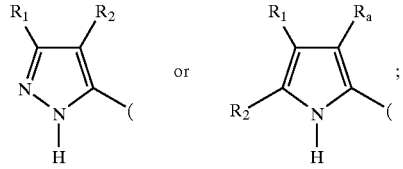

Ar is 1-naphthyl;

L is $C_{1-6}$ saturated or unsaturated branched or unbranched carbon chain wherein one or more C atoms are optionally replaced by O, N or S(O)$_m$; and wherein said linking group is optionally substituted with one to two oxo groups, $C_{1-4}$ alkyl optionally substituted by one or more halogen atoms;

or L is cyclopentenyl, cyclohexenyl, cycloheptenyl, each optionally substituted with an oxo group or 1–3 $C_{1-4}$ branched or unbranched alkyl or $C_{1-4}$alkoxy;

or L is phenyl, pyridine, furan or thiophene each being optionally independently substituted with 1–3 $C_{1-4}$ branched or unbranched alkyl, $C_{1-4}$alkoxy, cyano, di-($C_{1-3}$ alkyl)amino, $C_{1-6}$ alkyl-S(O)$_m$ or halogen;

wherein said cyclic group is optionally attached to a $C_{1-4}$ saturated or unsaturated branched or unbranched carbon chain wherein said carbon chain is in turn covalently attached to Q, said carbon chain is optionally partially or fully halogenated and wherein one or more methylene groups are optionally replaced by O, N or $S(O)_m$, wherein said methylene groups are further optionally independently substituted with 1–2 oxo groups and one or more $C_{1-4}$ branched or unbranched alkyl optionally substituted by one or more halogen atoms;

$R_1$ is $C_{3-4}$ alkyl branched or unbranched, cyclopropyl or cyclohexanyl optionally partially or fully halogenated and optionally substituted with one to three $C_{1-3}$ alkyl groups;

$R_3$ is selected from the group consisting of phenyl, pyridinyl each being optionally substituted with one to five groups selected from the group consisting of a $C_{1-6}$ branched or unbranched alkyl, phenyl, naphthyl, pyridinyl, $C_{1-6}$ branched or unbranched alkyl, cyclopropyl, cyclobutyl, cyclopentanyl, cyclohexanyl, cycloheptanyl, bicyclopentanyl, bicyclohexanyl, bicycloheptanyl, phenyl $C_{1-5}$ alkyl, naphthyl $C_{1-5}$ alkyl, halo, cyano, $C_{1-3}$ alkyloxy which may optionally be partially or fuilly halogenated, phenyloxy, naphthyloxy, pyridinyloxy, nitro, di-$(C_{1-3})$alkylamino, di-$(C_{1-3})$alkyl aminocarbonyl, $C_{1-5}$ alkyl-C(O)—$C_{1-4}$ alkyl, di-$(C_{1-3})$alkylamino-$C_{1-5}$ alkyl, di-$(C_{1-3})$alkylamino-S$(O)_2$, $R_4$—$C_{1-5}$alkyl, $R_5$—$C_{1-5}$ alkoxy, $R_6$—C(O)—$C_{1-5}$ alkyl and $R_7$—$C_{1-5}$ alkyl-N$(R_8)$—.

5. The process according to claim 4 wherein
L is:
O—$CH_2$—, O—$CH_2CH_2$, O—$CH_2CH_2CH_2$, O—$CH_2CH_2(CH_3)$, O—$CH_2(CH_3)CH_2$, $S(O)_mCH_2$, $S(O)_mCH_2CH_2$, $S(O)_mCH_2CH_2CH_2$, $CH_2$, $CH_2CH_2$, $CH_2CH_2CH_2$, O—$CH_2C(O)$, HC≡C—$CH_2$ or HC≡C—$H_2O$;
and Q is N-morpholino.

6. The process according to claim 5 wherein L is O—$CH_2CH_2$.

7. The process according to claim 6 wherein:

in step 1):

the base is selected from triethylamine, diisopropylethylamine, N-methylpyrrolidine, DBU, DMAP, N-methylmorpholine, pyridine and methyl pyridine;

the polar non-protic organic solvent selected from NMP, acetonitrile, DMF, DMAC and DMSO;

the temperature is about 80° C.;

the reaction time is 4–10 hours;

$R_b$ is 2,2,2-trichloroethyl;

in step 2):

Y—$R_3$ is present in about a two-fold molar excess, wherein Y is $B(OH)_2$;

the base is triethylamine or pyridine and is present in about a two-fold molar excess;

the catalyst is $Cu(OAc)_2$, $(Cu(OH).TMEDA)_2Cl_2$ or $CuCO_3.Cu(OH)_2$ and present at about a 1.5 molar excess;

the solvent is selected from methylene chloride, 1,4-dioxane, N-methylpyrrolidinone, THF and DMF.

8. The process according to claim 7 wherein:

in step 1):

the base is diisopropylethylamine;

the polar non-protic organic solvent is DMSO;

in step 2):

the base is pyridine;

the catalyst is $Cu(OAc)_2$;

the solvent is methylene chloride.

* * * * *